(12) United States Patent
Speier et al.

(10) Patent No.: US 6,232,778 B1
(45) Date of Patent: May 15, 2001

(54) METHOD FOR OBTAINING NMR BOUND FLUID VOLUME USING PARTIAL POLARIZATION

(75) Inventors: Peter Speier, Stafford; Steven F. Crary, Sugar Land, both of TX (US); Robert L. Kleinberg; Charles Flaum, both of Ridgefield, CT (US)

(73) Assignee: Schlumberger Technology Corporation

( * ) Notice: Subject to any disclaimer, the term of this patent is extended or adjusted under 35 U.S.C. 154(b) by 0 days.

(21) Appl. No.: 09/096,320

(22) Filed: Jun. 11, 1998

(51) Int. Cl.$^7$ .................................................. G01V 3/00
(52) U.S. Cl. .............................................................. 324/303
(58) Field of Search ............................................. 324/303

(56) References Cited

U.S. PATENT DOCUMENTS

| | | |
|---|---|---|
| 5,023,551 | 6/1991 | Kleinberg et al. . |
| 5,280,243 * | 1/1994 | Miller .................................. 324/303 |
| 5,389,877 | 2/1995 | Sezginer et al. . |
| 5,486,762 * | 1/1996 | Freedman et al. ................... 324/303 |
| 5,596,274 | 1/1997 | Sezginer . |
| 6,005,389 * | 12/1999 | Prammer ............................. 324/303 |

FOREIGN PATENT DOCUMENTS

| | | |
|---|---|---|
| 0544585 | 3/1996 | (EP) . |
| WO 97/34167 | 9/1997 | (WO) . |
| WO 98/29639 | 7/1998 | (WO) . |

OTHER PUBLICATIONS

Coates, G. R., Marschall, D. and Mardon, D., "A New Characterization of Bulk–Volume Irreducible Using Magnetic Resonance", SPWLA 38$^{th}$ Annual Logging Symposium, Jun. 15–18, 1997, pp. 1–14.

Kleinberg, R. L. and Boyd, A., "Tapered Cutoffs for Magnetic Resonance Bound Water Volume", SPE 38737, presented at 1997 SPE Annual Technical Conference and Exhibition, San Antonio, Texas, Oct. 5–8, 1997.

* cited by examiner

*Primary Examiner*—Christine K. Oda
*Assistant Examiner*—Tiffany A. Fetzner
(74) *Attorney, Agent, or Firm*—John J. Ryberg; Brigitte L. Jeffery

(57) ABSTRACT

The present invention provides methods for determining the bound fluid volume (BFV) of a formation utilizing nuclear magnetic resonance (NMR) techniques in which less than full polarization occurs and in which less than a complete NMR distribution is acquired. The effect of the polarizing static magnetic field is shortened in time by applying a shortened wait time between NMR measurements so that only the bound fluid of the formation is polarized. The shortened wait time is effectuated by early application of the oscillating magnetic field to the formation which, in conjunction with a limited number of refocusing pulses, induces signals in the formation that are measured by the NMR tool. The peak amplitude of these signals corresponds to the BFV. The present invention provides information so that a partial polarization calculation curve in $T_2$ lies almost equally between an empirical tapered cutoff curve and a theoretical tapered cutoff curve. Moreover, because no $T_2$ information must be acquired, the method is especially suited for logging-while-drilling operations, where the drill string moves uncontrollably during the NMR measurement.

29 Claims, 5 Drawing Sheets

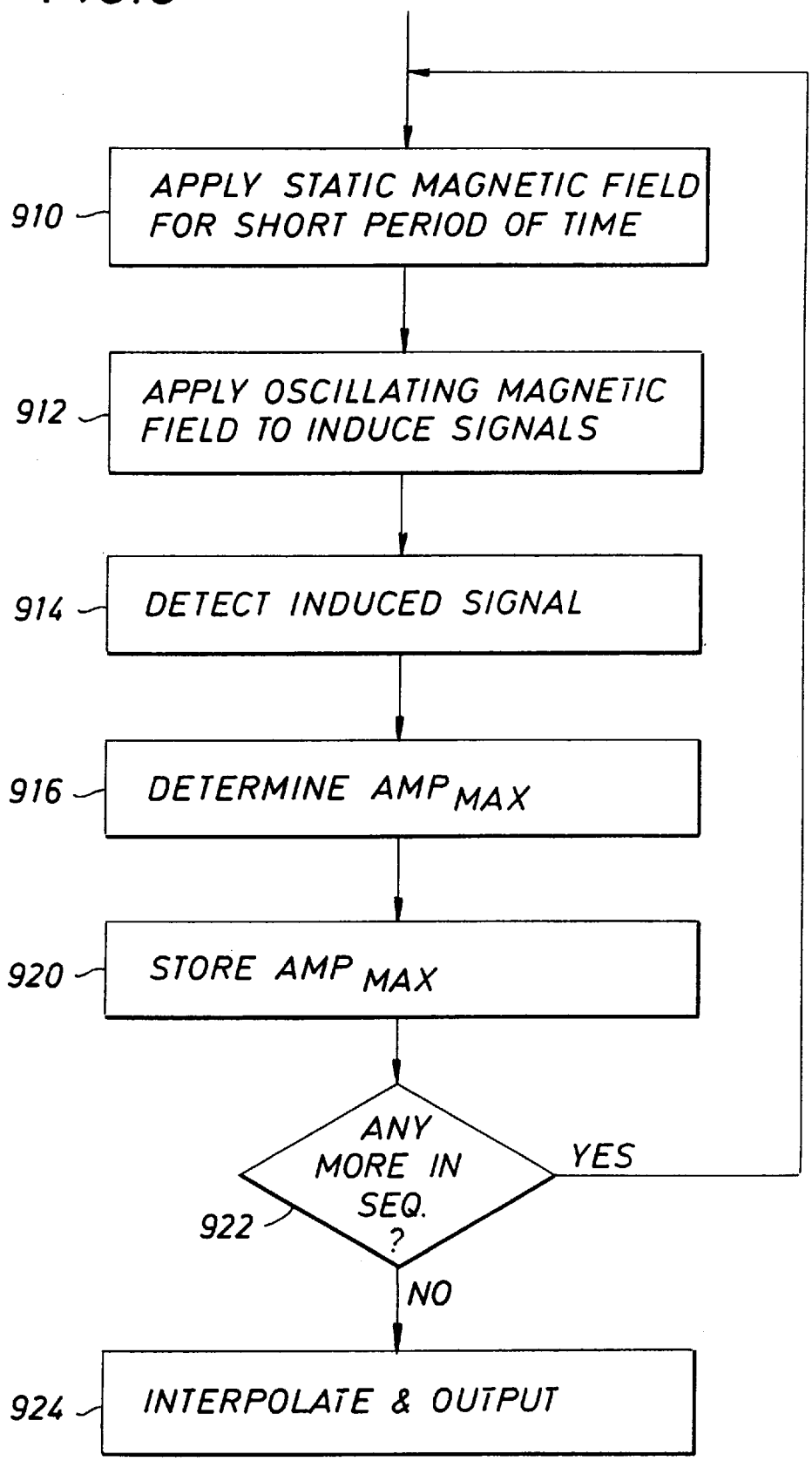

METHOD FOR OBTAINING NMR BOUND FLUID VOLUME USING PARTIAL POLARIZATION

FIELD OF THE INVENTION

This invention relates to the field of well logging of earth boreholes and, more particularly, to methods for obtaining bound fluid volume from nuclear magnetic resonance measurements using partial polarization.

BACKGROUND OF THE INVENTION

Well logging provides various parameters that may be used to determine the "quality" of a formation from a given borehole. These parameters include such factors as: resistivity, porosity, permeability and bound fluid volume (BFV). The parameters may be used to determine the amount of hydrocarbons present within the formation, as well as provide an indication as to the difficulty in extracting those hydrocarbons from the formation. BFV, in general, represents the volume of fluid that normally cannot be extracted from the formation (versus free fluid volume—the volume of fluid that will flow through the pores of the formation and thus, may be extracted). BFV is therefore, an important factor in determining whether a specific well site is commercially viable.

There are various known techniques for determining BFV. For example, it is known to apply nuclear magnetic resonance (NMR) techniques to measure BFV. NMR measurements, in general, are accomplished by causing the magnetic moments of nuclei in a formation to precess about an axis. The axis about which the nuclei precess may be established by applying a strong, polarizing, static magnetic field ($B_0$) to the formation, such as through the use of permanent magnets. This field causes the proton spins to align in a direction parallel to the applied field (this step, which is sometimes referred to as the creation of longitudinal magnetization, results in the nuclei being "polarized"). Polarization does not occur immediately, but instead grows in accordance with a time constant $T_1$, as described more fully below, and may take as long as several seconds to occur (even up to about eight seconds). After sufficient time, a thermal equilibrium polarization ($M_\infty$) parallel to $B_0$ has been established (i.e., $M_\infty$ is proportional to $B_0$)

Next, a series of radio frequency (RF) pulses are produced so that an oscillating magnetic field, $B_1$, is applied. The first RF pulse (referred to as the 90° pulse) must be strong enough to rotate the magnetization from $B_0$ substantially into the transverse plane (i.e., transverse magnetization). The rotation angle is given by:

$$\alpha = \gamma B_1 t_p \quad (1)$$

(where $t_p$ is the pulse length) and is adjusted to be 90°. Additional RF pulses, preferably a $\alpha$=180° (referred to as 180° pulses), are applied to create a series of spin echos. The frequency of the RF pulses is chosen to excite specific nuclear spins of a particular region of the sample that is being investigated. The rotation angles of the RF pulses are adjusted to be 90° and 180° in the center of this region.

Two time constants are associated with the relaxation processes of the longitudinal and transverse magnetization. These time constants characterize the rate of return to thermal equilibrium of the magnetization components following the application of each 90° pulse. The spin-lattice relaxation time ($T_1$) is the time constant for longitudinal magnetization to return to its thermal equilibrium value $M_\infty$ in the static magnetic field. The spin-spin relaxation time ($T_2$) is the time constant for the transverse magnetization to return to its thermal equilibrium value which is zero. In addition, $B_0$ is typically inhomogeneous and the transverse magnetization decays with the shorter time constant $T_2^*$, where:

$$\frac{1}{T_2^*} = \frac{1}{T_2} + \frac{1}{T'} \quad (2)$$

but the part decaying with T', which is due to the inhomogeneous $B_0$, can be recovered by refocusing pulses that produce the echos.

The most common method for determining BFV involves determining the entire fully polarized $T_2$ distribution and then computing results based on $T_2$ values less than a fixed cutoff value (e.g., 33 milliseconds for sandstone). The portion of protons with $T_2$'s smaller than the fixed cutoff represents the BFV, while the portion of protons with $T_2$'s larger than the fixed cutoff represents the amount of free fluid in the formation.

Another known method for calculating BFV determines the entire $T_2$ distribution for a given sample, and then computes the amplitude of the signal components with $T_2$ values less than the "free fluid" cutoff value (or relaxation cutoff time). Instead of the traditional fixed cutoff, a tapered cutoff is theoretically determined that accounts for bound fluid volume lining large pores that would otherwise be considered to be free or extractable (see, R. L. Kleinberg et al., "Tapered Cutoffs for Magnetic Resonance Bound Fluid Volume," *Society of Petroleum Engineers*, Doc. No. SPE 38737, 1997) (the "Kleinberg theoretical analysis"). For example, previous determinations of bound fluid assume that the bound fluid occupies small pores and free fluid occupies large pores. It was then assumed that the large pores would empty so that any fluid therein was free fluid, not bound fluid. The Kleinberg theoretical analysis, however, found that under certain circumstances, such as in clean well-sorted sands and carbonates where fixed cutoff computations provide low bound fluid results, the tapered cutoff provides a more accurate measure of BFV.

Another way to determine BFV using a tapered cutoff is based on empirically derived tapered cutoffs rather than the theoretically determine d tapered cutoff described above. The derived tapered cutoff relates each relaxation time to a specific fraction of capillary bound water, assuming that each pore size has an inherent irreducible water saturation (see, G. R. Coates et al., "A New Characterization of Bulk-Volume Irreducible Using Magnetic Resonance," *SPWLA 38th Annual Logging Symposium*, Jun. 15–18, 1997) (the "Coates empirical analysis"). The Coates empirical analysis utilized permeability models that do not rely on a specific model of pore geometry t o relate irreducible water saturation ($S_{WIRR}$) to the $T_2$ distribution as follows:

$$\frac{1}{S_{WIRR}} = mT_2 + b \quad (3)$$

(where m and b a re empirical factors used for calibration of empirical data sets) which was then applied to different values of m with b=1, and different values of b with m=0.0618. In both the Kleinberg theoretical analysis and the Coates empirical analysis, the entire $T_2$ distribution is used (rather than the cutoff method) to determine BFV, which is a direct output of the inversion of the echo data.

Another known method for calculating BFV using NMR is the fixed cutoff method which is described in commonlyassigned, Sezginer et al. U.S. Pat. No. 5,389,877 (Sezginer). Sezginer describes using NMR techniques in which a short train of spin echos (i.e., j echoes) are used to obtain a sharp cutoff (i.e, the fixed cutoff relaxation time $T_C$) that can be used to determine the producible volume in a borehole by measuring bound fluid and subtracting it from total porosity. These NMR techniques apply a weighted sum of the echos to determine BFV as follows:

$$\overline{BFV} = \sum_{j=1}^{J} w_j echo_j \quad (4)$$

(where $w_j$ is a weighting factor chosen to weight different $T_2$ components differently to sharpen (i.e., make steeper) the produced cutoff curve, and the overbar represents an estimate of BFV). The estimator of BFV is a linear function that acts on the relaxation-time distribution:

$$\overline{BFV} = \int_0^\infty f(T_1)\alpha(T_1)dT_1 \quad (5)$$

where $f(T_1)$ is a weighting function as follows:

$$f(T_1) = [1 - e^{-T_r/T_1}] \sum_{j=1}^{J} w_j \exp\left(\frac{-2jt_{cp}(T_1/T_2)}{T_1}\right) \quad (6)$$

(where $T_r$ is the recovery time before a CPMG sequence, and $t_{cp}$ is the Carr-Parcell spacing). $f(T_1)$ is approximately equal to 0 if $T_1$ is greater than $T_C$, and approximately equal to 1 if $T_1$ is less than $T_C$. Sezginer assumes that the $T_1/T_2$ ratio is approximately constant, being about unity for bulk water samples and about 1.5 for water saturated sandstones. A potential problem with the sharp cutoff of Sezginer may occur if the echo decays faster than predicted, for example, if motion of the measuring probe occurs during measurements. Under these conditions, the resultant data may be degraded.

While Sezginer assumes that the $T_1/T_2$ ratio is approximately constant, the $T_1/T_2$ ratio must be considered when a shortened wait time between NMR experiments (e.g., as set forth in Sezginer) is used in determining BFV. For example, it is known that the NMR signal from a fluid is proportional to the hydrogen index (HI) and $T_1$ Effect (TOE Factor) as described by Kleinberg & Vinegar in "NMR Properties for Reservoir Fluids," *The Log Analyst*, Nov.–Dec. 1996. Kleinberg and Vinegar provide that the TOE Factor is defined as:

TOE Factor=[1−exp(−$t_r$/$T_1$)] (7)

(where $t_r$ is the wait time between NMR measurements and $T_1$ is the longitudinal relaxation time, as described above). Kleinberg and Vinegar also showed that the signal for a given $T_2$ may be determined as:

S($T_2$)=$V_{water}$($T_2$)×$HI_{water}$×[1−exp (−$t_r$/$T_{1water}$)]

+$V_{oil}$($T_2$)×$HI_{oil}$×[1−exp(−$t_r$/$T_{1oil}$)]

+$V_{gas}$($T_2$)×$HI_{gas}$×[1−exp(−$t_r$/$T_{1gas}$)] (8)

where $T_2$ is the transverse relaxation time as described above. $T_1$ is a different function of $T_2$ for each fluid. By factoring the ratio of $T_1/T_2$, the TOE Factor can be calculated based on $T_2$ instead of $T_1$ as follows:

TOE Factor =[1−exp(−$t_r$/(Ratio*$T_2$))] (9)

where Ratio is the ratio of $T_1/T_2$ which is expected to be about 1.5 for clay and capillary bound fluid formations, but may be equal to 1 under other conditions. Applying this ratio results in polarization expressions (i.e., equations 7 and 9) that are based on either $T_1$ or $T_2$.

Most of the above-described methods for determining BFV suffer from at least the common problem that the entire $T_2$ distribution must be obtained (for example, Sezginer, on the other hand, utilizes only part of the $T_2$ distribution). Under some circumstances, for example, in logging-while-drilling, it simply may not be possible to acquire the necessary $T_2$ distribution, or the motion of logging-while-drilling may degrade the measured data (e.g., such as when the techniques of Sezginer are applied). Under other circumstances, such as when high logging speed is required, it may not be practical to obtain the entire $T_2$ distribution. Under still other circumstances, it only may be practical to obtain the initial amplitude of the NMR signal, in which case, known methods for determining BFV are not available. Moreover, well logging typically is a time intensive task, requiring large expenditures of effort to acquire well data.

For at least the foregoing reasons, it is an object of the present invention to provide methods for determining BFV utilizing NMR techniques when less than a substantial part of the $T_2$ distribution is available.

It is also an object of the present invention to provide methods for determining BFV utilizing NMR techniques when high logging speed is required.

It is a further object of the present invention to provide methods for determining BFV utilizing NMR techniques in which only the initial amplitude of the NMR signal is obtained.

It is a still further object of the present invention to provide methods for determining BFV utilizing NMR techniques in which well logging time is reduced.

SUMMARY OF THE INVENTION

These and other objects of the invention are accomplished in accordance with the principles of the invention by providing methods for determining the bound fluid volume (BFV) of a formation utilizing nuclear magnetic resonance (NMR) techniques in which less than full polarization occurs and in which less than a substantial part of the NMR distribution is acquired. The preferred embodiments include methods in which a shortened wait time is utilized so that only part of the formation is polarized and a limited number of echo pulses are utilized to determine BFV. By only polarizing the bound fluid of the formation and by only requiring a limited number of echo pulses, the NMR methods of the present invention are capable of providing BFV at high logging speeds, such as those in excess of 1,800 feet per hour without a substantial degradation of vertical response. Moreover, the techniques of the present invention also may be used during logging-while-drilling operations, at least because of the shortened necessary duration of the echo train that results from measurements of partial polarization instead of $T_2$ decay.

The methods of the present invention utilize a significantly shortened wait time $t_r$, where $t_r$ is the time from the last 180° pulse of one NMR experiment until the application of the 90° pulse to start the next NMR experiment—persons skilled in the art will appreciate that, in the circumstance where only single pulse sequences are utilized (e.g., while the drill pipe is moving), the shortened wait time is defined from the time the spins enter the static magnetic field. The shortened wait time is selected so that the static magnetic field $B_0$ is only applied for a short period of time before the next NMR experiment begins. This results in $B_0$ polarizing only the bound fluid in the formation, rather than the bound and free fluid, so that the measured amplitude represents the actual BFV of the part of the formation being analyzed.

The length of time it takes to run any NMR experiment is mainly determined by the wait time, which is greater than the time required to measure the echos. Therefore, because of the shortened wait time, the partial polarization NMR experiments of the present invention always take less time to run than conventional NMR experiments. This results in the ability to stack more experiments—i.e., perform and add up more experiments in a given period of time—resulting in an improved signal-to-noise ratio (SN) (because SN is proportional to the square root of the number of acquisitions (n)). The NMR experiments of the present invention provide information so that a partial polarization calculation curve in $T_2$ lies almost equally between the Kleinberg and Coates tapered cutoff curves.

Further features of the invention, its nature and various advantages will be more apparent from the accompanying drawings and the following detailed description of the preferred embodiments.

BRIEF DESCRIPTION OF THE DRAWINGS

FIG. 9 is a flow chart illustrating steps for another embodiment of determining bound fluid volume (BFV) in accordance with the principles of the present invention.

DETAILED DESCRIPTION OF THE PREFERRED EMBODIMENTS

Figure 1:
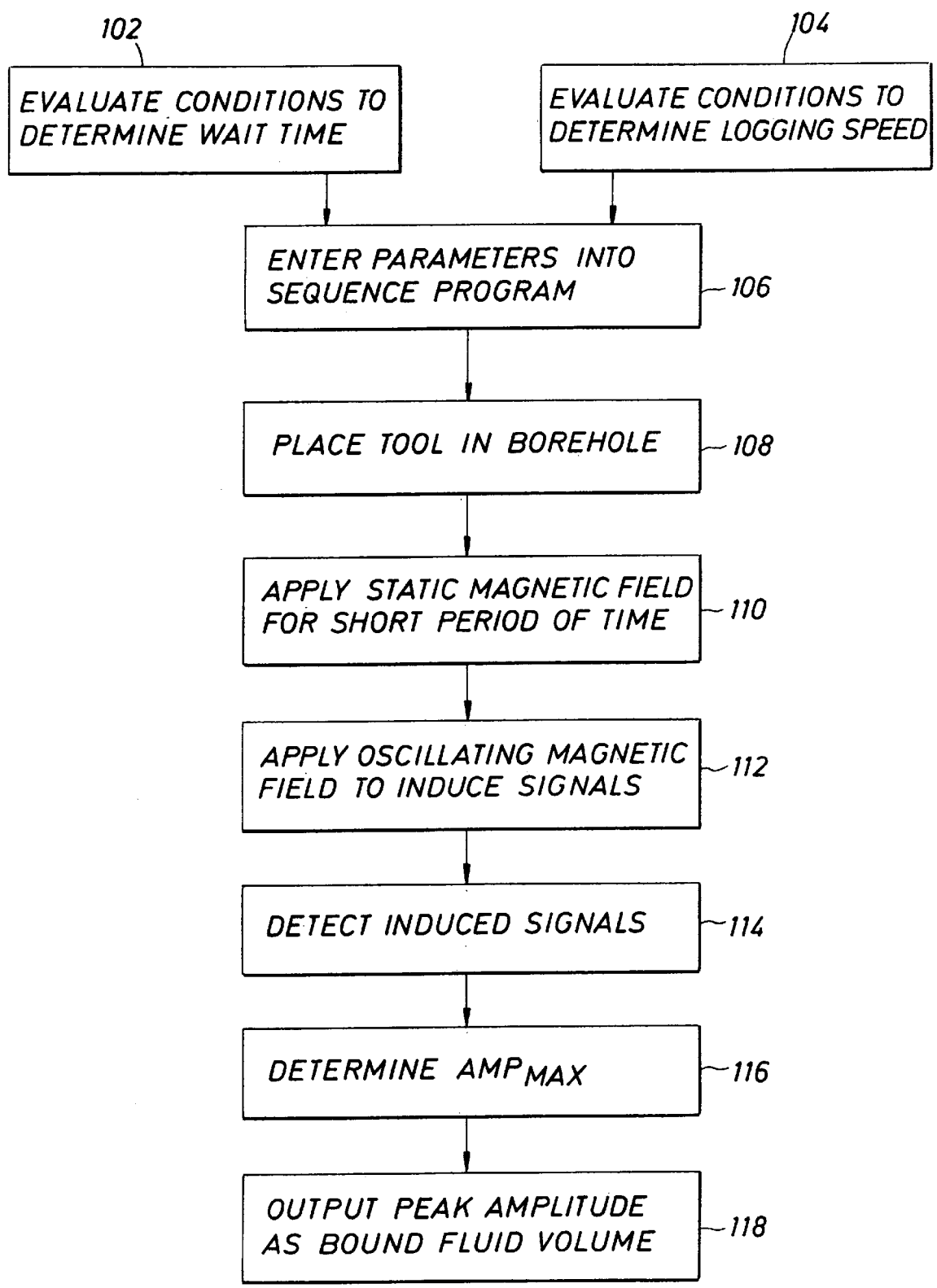
FIG. 1 is a flow chart illustrating steps for determining bound fluid volume (BFV) in accordance with the principles of the present invention.

Various well known techniques exist for determining many of the parameters associated with the production of hydrocarbons from ground formations using nuclear magnetic resonance (NMR) tools. These parameters include porosity $\phi$ (the fraction of the formation per unit volume occupied by pore spaces), permeability k (the ease with which fluid passes through the formation), free fluid volume FFV (the fluid within the formation that is capable of being extracted through the pores), and bound fluid volume BFV (the fluid within the formation that is trapped inside pores and will not flow out during the extraction process). The present invention describes methods for determining BFV based on a limited quantity of acquired data.

Typical NMR techniques for determining various geological parameters include a lengthy, time consuming process in which $T_2$ distributions with full polarization of almost all $T_1$ components are obtained and analyzed. The present invention provides methods for determining BFV utilizing NMR techniques in which only partial polarization is performed so that recording fully polarized, complete, $T_2$ distributions are unnecessary.

In accordance with the principles of the present invention, a substantially short wait time is utilized between NMR experiments so that the static magnetic field $B_0$ only polarizes the bound fluid of the formation (as compared to traditional NMR experiments where the wait time is extensive to insure that the applied static magnetic field $B_0$ has sufficient time to fully polarize the part of the formation being analyzed before the application of the oscillating magnetic field—a time typically up to five times $T_{1MAX}$ (i.e., the time required to insure that all of the fluid—both bound fluid and free fluid—in the formation is polarized), where $T_{1MAX}$ is the largest $T_1$ value present in the sample).

In addition, because only the initial amplitude of the echo train is measured, a substantially limited number of echos are required to measure induced magnetic signals (conventional NMR techniques typically apply hundreds of echos to produce a complete $T_2$ distribution). Moreover, the short wait time together with the reduced number of echos causes the NMR experiment to take less time than traditional NMR experiments. The short experiment time enables the operator to conduct more experiments in a given time period resulting in logging data having a significantly improved signal-to-noise ratio. The improvement in signal-to-noise ratio is often on the order of at least three times over conventional techniques, at least because the length of time to run one partial polarization NMR measurement is typically at least ten times shorter than a conventional measurement. Thus, at least ten times more partial polarization NMR experiments may be run for a given period of time than conventional NMR experiments and the signal-to-noise ratio scales with the square root of n, where n is the number fo experiments.

FIG. 1 shows a flow diagram that generally illustrates methods for determining BFV in accordance with the principles of the present invention. Initial preparations may occur in step 102 to determine the wait time $t_r$ that is used in the NMR measurement. As described above, the methods of the present invention require that $t_r$ be substantially shorter than $t_r$ in conventional measurements. For example, it is known that $t_r$ for conventional NMR measurements in rocks is on the order of about one to eight seconds (1–8 sec.). In accordance with the present invention, however, $t_r$ is always less than one-tenth of one second, and, for experiments in sandstones, is preferably on the order of ten to sixty milliseconds (10–60 msec.). The determination of $t_r$ depends on the petrophysical properties of the formation being sampled. For example, wait time $t_r$ is less for sandstones than for carbonates. Thus, in general, the determination of $t_r$ is empirical, based on known information about the formation being sampled.

Initial preparations may also occur in step 104 to determine the logging speed of the instant NMR measurement. For example, while it may be preferred to acquire full $T_2$ distributions (because, for example, a full distribution is more useful for post-collection data analysis), circumstances may be such that it is not possible to obtain full distributions. Additionally, if only BFV is required, the partial polarization techniques of the present invention enable the logging operator to run the NMR measurement at high speeds of approximately 1800 feet per hour, versus traditional NMR well logging speeds, in order to save time. Moreover, the same techniques enable the operator to conduct BFV NMR experiments during logging-while drilling operations without data degradation even though it is likely that the NMR tool will experience lateral motion during NMR experiments.

Once the operational parameters have been determined, they may be entered into the NMR tool sequence program in step 106. The logging operator, in step 108, places the tool in the borehole. Persons skilled in the art will appreciate that the partial polarization NMR experiments of the present invention simply may begin at step 108, instead of step 102. Prior to the introduction of the NMR tool into the borehole, the spins of the nuclei will generally be aligned with the earth's naturally occurring magnetic field. The presence of the NMR tool in step 110, and its static magnetic field $B_0$, however, causes the spins to begin to be aligned with $B_0$. In accordance with the present invention, the wait time $t_r$ between NMR experiments is substantially short so that the application of $B_0$ is limited to polarizing the bound fluid of the formation, as compared to traditional NMR borehole measurements (as described above).

After the significantly shortened wait time $t_r$ has passed, in step 112, an oscillating magnetic field $B_1$ is applied. The application of $B_1$ causes the spins to tip into the transverse plane, at which point they begin to precess (at a frequency equal to the Larmor frequency). The application of $B_1$, as described in more detail with respect to FIG. 2, induces the protons to emit magnetic energy that may be measured by the NMR tool, in step 114. The measured signals are then analyzed, in step 116, to determine the initial amplitude ($AMP_{MAX}$) of the echo train at "time zero" (where "time zero" is the point of origin of the echo train whose position within the excitation pulse is understood by persons skilled in the art). The determination of $AMP_{MAX}$ may be performed by known techniques, such as extrapolation whereby $AMP_{MAX}$ (the amplitude at time t=0) is extrapolated backwards from the measured NMR echos (e.g., the echos from time=1, 2, 3, 4, 5 and 6). The extrapolation should be insensitive to variations in the decay rate of the echo train (i.e., using a porosity estimator). Finally, in step 118, $AMP_{MAX}$ is provided as an output that corresponds to the bound fluid volume (BFV).

Figure 2:
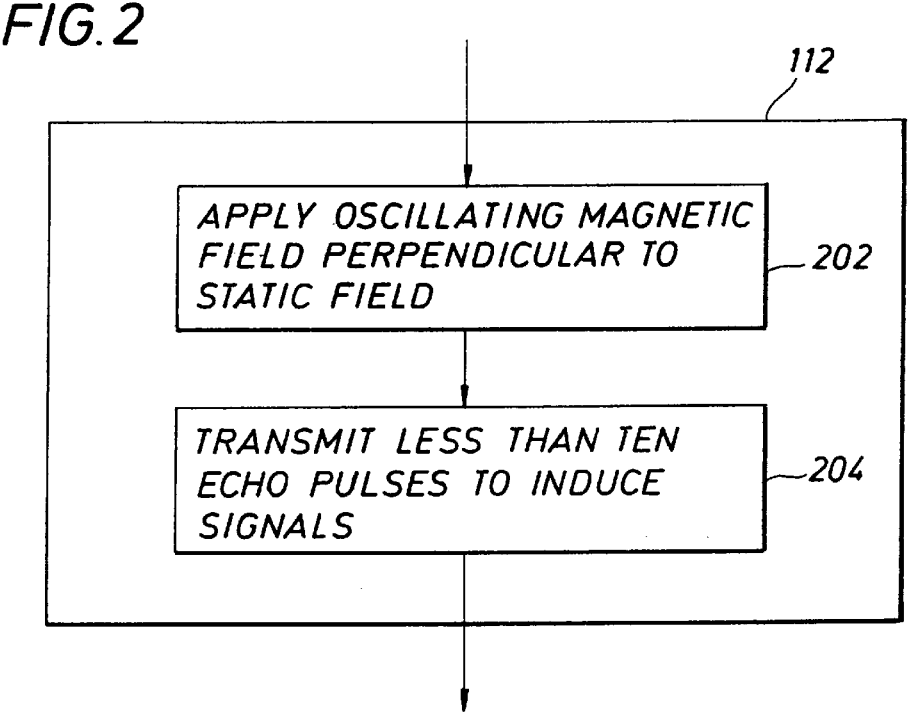
FIG. 2 is a flow chart illustrating a preferred embodiment of the method of determining BFV of FIG. 1 in accordance with the principles of the present invention.

The application of the oscillating field $B_1$ is shown in more detail in FIG. 2. The first step in applying $B_1$ is the application of an oscillating magnetic field perpendicular to the static magnetic field $B_0$ (i.e., the 90° pulse), in step 202. This signifies the "beginning" of a single NMR measurement and the end of the significantly shortened wait time $t_r$. As the spins begin to precess, they generate a small magnetic field that can be detected by the NMR equipment (i.e., step 114 above). However, because the protons quickly lose synchronization, the net magnetization is quickly reduced. In order to obtain accurate NMR measurements, in step 204, one or more rephasing pulses (i.e., the 180° pulses) are applied that are perpendicular to static magnetic field $B_0$. The rephasing pulses induce additional magnetic signals from the protons (i.e., spin-echos) that are measured. The shortened wait time $t_r$ begins after the application of the last rephasing pulse for a given NMR experiment, and ends when the next 90° pulse is applied.

In accordance with the principles of the present invention, NMR measurements of BFV may be accomplished with a single echo pulse in step 204. It may be preferable, however, to obtain on the order of five or six echo pulses to improve signal quality. In any case, the present invention provides that BFV measurements may be obtained where less than ten echo pulses are generated, as compared to traditional NMR measurements in which hundreds or thousands of echo pulses are utilized to acquire a full $T_2$ distribution.

Additional advantages of the present invention result from the shortened wait time $t_r$ and the reduced number of echo pulses. These two factors combine to provide very short duration NMR experiments that provide the opportunity to stack significantly more NMR experiments in a given time period than conventional NMR experiments. The signal-to-noise ratio (SN) of the acquired data significantly improved by this process because SN is proportional to the square root of the number of acquisitions. Thus, BFV measurements obtained in accordance with this invention have superior signal-to-noise ratios as compared with conventional BFV measurements.

Figure 3:
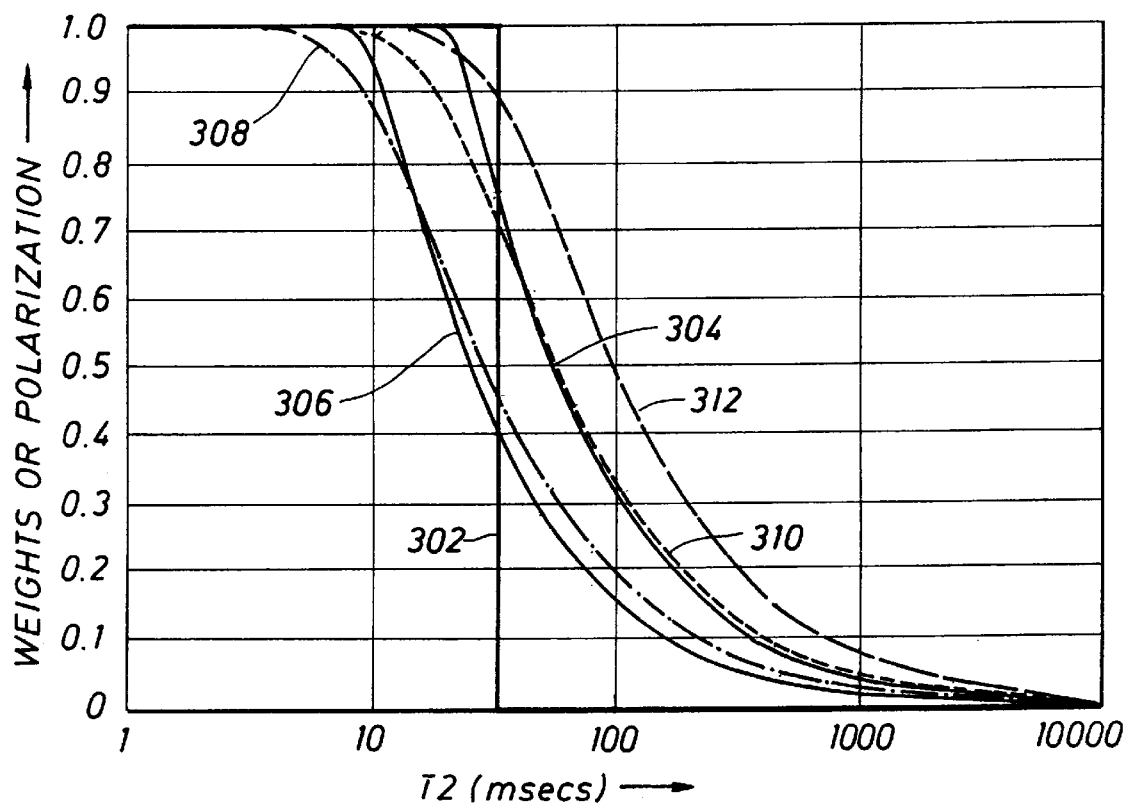
FIG. 3 is a graph showing a comparison of polarization versus $T_2$ as determined for two theoretical tapered cutoff analyses (i.e., Kleinberg theoretical analyses) and several partial polarization determinations in accordance with the present invention.

FIGS. 3–7 show various comparisons of partial polarization cutoffs versus the empirical and theoretical tapered cutoff calculations. FIG. 3 shows polarization versus $T_2$ for a traditional fixed $T_2$ cutoff (i.e., $T_{2cutoff}$) of 33 milliseconds (i.e., for sandstone) on curve 302. Curve 304 represents a tapered $T_2$ cutoff derived theoretically based on $T'=0.5*T_{2cutoff}$, while Curve 306 represents a tapered $T_2$ cutoff derived empirically based on $T'=0.22*T_{2cutoff}$. The dashed curves are partial polarization curves in $T_2$ (according to equation 9) calculated for different wait times $t_r$ and a ratio $T_1/T_2$ of 1.5. For example, curve 308 shows the partial polarization curve in $T_2$ for $t_r$ equal to 30 milliseconds; curve 310 shows the partial polarization curve in $T_2$ for $t_r$ equal to 60 milliseconds; and curve 312 shows the partial polarization curve in $T_2$ for $t_r$ equal to 100 milliseconds. FIG. 3 clearly shows the correlation between the theoretical tapered cutoff in $T_2$ and the partial polarization cutoff according to the present invention expressed using equation 9 in $T_2$ when $t_r$ equals 60 milliseconds; and also the correlation between the empirical tapered $T_2$ cutoff and the partial polarization cutoff according to the present invention expressed using equation 9 in $T_2$ when $t_r$ equals 30 milliseconds for a $T_1/T_2$ ratio of 1.5.

For each of curves 308, 310 and 312, partial polarization is based on Equation (7) above, which shows that polarization corrections may be solely a function of $T_1$, however, because the curves in FIG. 3 are plotted against $T_2$, the $T_1/T_2$ ratio is used as described above in accordance with Equation (9). Thus, only a knowledge of $T_1$ is necessary to practice the partial polarization techniques of the present invention and the time required to obtain full $T_2$ distributions may be avoided.

The tapered cutoff calculations are based on the "Kleinberg theoretical analysis," which recites BFV as follows:

$$FV = \sum_{T_{2i}=T_{2\min}}^{T'} m(T_{2i}) + \sum_{T_{2i}=T'}^{T_{2\max}} m(T_{2i}) \left( \frac{2T'}{T_{2i}} - \left(\frac{T'}{T_{2i}}\right)^2 \right) \quad (10)$$

where $m(T_{2i})$ is the $T_2$ distribution of fully saturated rock and $T_2=0.5T_{2cutoff}$, arid where the tapered cutoff data shown in FIG. 3 is plotted from the function within the outermost parenthesis of equation (10).

Figure 4:
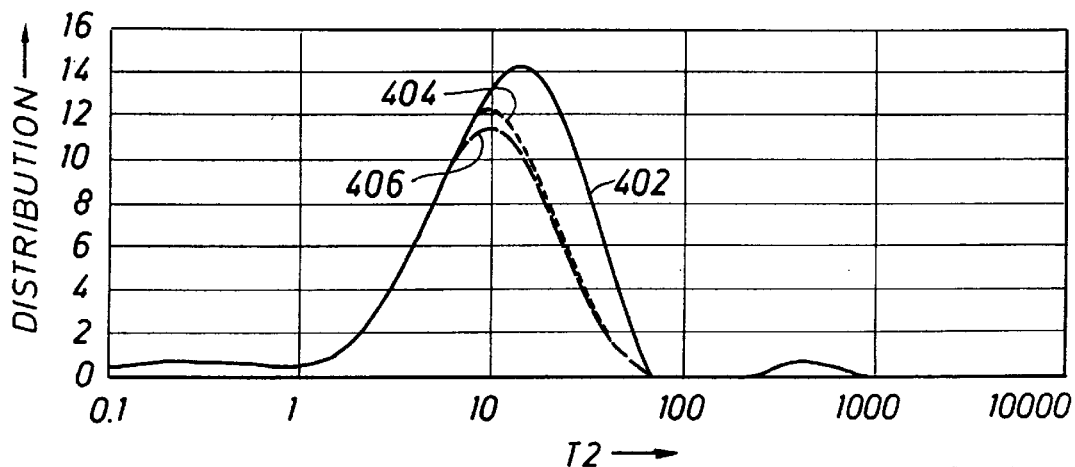
FIG. 4 is a graph showing a comparison of $T_2$ distributions for a low permeability sample as determined for a theoretical tapered cutoff analysis (i.e., Kleinberg theoretical analysis) and for a partial polarization analysis in accordance with the present invention.

FIG. 4 shows an original $T_2$ distribution for a low permeability sample compared to a tapered $T_2$ cutoff calculation and a partial polarization calculation made using equation 9 in $T_2$. Curve 402 represents an actual laboratory $T_2$ distribution obtained from a silty sandstone sample. NMR analysis of the sample showed it to have a porosity of 31.80 pu and a permeability of 6.39 md. Curve 404 represents a tapered cutoff calculation of $T_2$ based on T'=0.22*$T_{2cutoff}$, where $T_{2cutoff}$ is 33 milliseconds (i.e., the fixed cutoff). Curve 404 results in a tapered $T_2$ cutoff calculation for BFV of 25.42 pu. Curve 406 represents a partial polarization curve in $T_2$ according to equation 9 with a wait time $t_r$ of 30 milliseconds. Curve 406 results in a partial polarization calculation in $T_2$ for BFV of 25.42 pu—within 0.01 pu of the value for the tapered $T_2$ cutoff.

Figure 5:
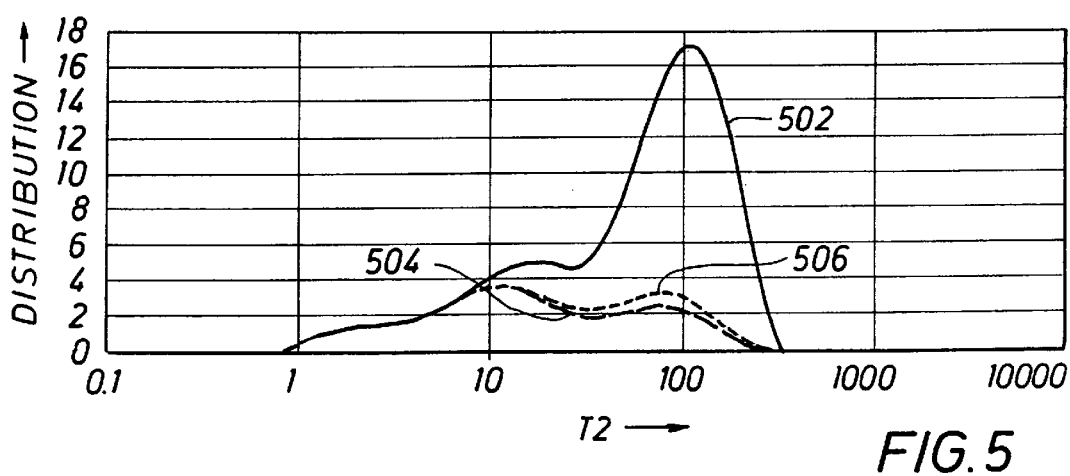
FIG. 5 is a graph showing a comparison of $T_2$ distributions for a high permeability sample as determined for a theoretical tapered cutoff analysis (i.e., Kleinberg theoretical analysis) and for a partial polarization analysis in accordance with the present invention.

FIG. 5 shows an original $T_2$ distribution for a high permeability sample compared to a tapered $T_2$ cutoff calculation and a partial polarization measurement in $T_2$. Curve 502 represents an actual laboratory $T_2$ distribution obtained from a sandstone sample. NMR analysis of the sample showed it to have a porosity of 33.70 pu and a permeability of 154.36 md. Curve 504 represents a tapered cutoff calculation of $T_2$ based on T'=0.22*$T_{2cutoff}$, where $T_{2cutoff}$ is 33 milliseconds (i.e., the fixed cutoff). Curve 504 results in a tapered $T_2$ cutoff calculation for BFV of 11.07 pu. Curve 506 represents a partial polarization curve in $T_2$ according to equation 9 with a wait time $t_r$ of 30 milliseconds. Curve 506 results in a partial polarization calculation in $T_2$ for BFV of 12.06 pu—within 0.99 pu of the value for the tapered $T_2$ cutoff. Thus, for both high and low permeability formations, the BFV results from tapered $T_2$ cutoff and partial polarization in $T_2$ are within 1 pu of each other.

Figure 6:
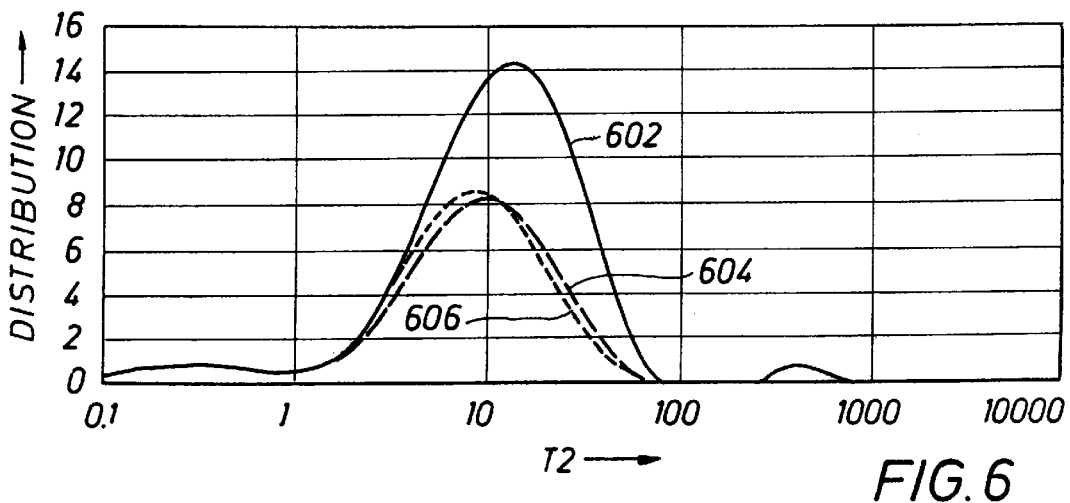
FIG. 6 is a graph showing another comparison of $T_2$ distributions for a low permeability sample as determined for an empirical tapered cutoff analysis (i.e., Coates empirical analysis) and for a partial polarization analysis in accordance with the present invention.

FIG. 6 shows an original $T_2$ distribution for a low permeability sample compared to an empirical tapered $T_2$ cutoff calculation and a partial polarization distribution (in accordance with equation 9) in $T_2$. Curve 602 represents an actual laboratory $T_2$ distribution obtained from a silty sandstone sample. NMR analysis of the sample showed it to have a porosity of 31.80 pu and a permeability of 6.39 md. Curve 604 represents an empirical tapered cutoff calculation of $T_2$ based on m=0.0618 and b=1. Curve 604 results in an empirical tapered $T_2$ cutoff calculation for BFV of 19.19 pu. Curve 606 represents a partial polarization distribution (in accordance with equation 9) in $T_2$ with a wait time $t_r$ of 15 milliseconds. Curve 606 results in a partial polarization calculation in $T_2$ for BFV of 19.24 pu—within 0.05 pu of the value for the tapered $T_2$ cutoff.

Figure 7:
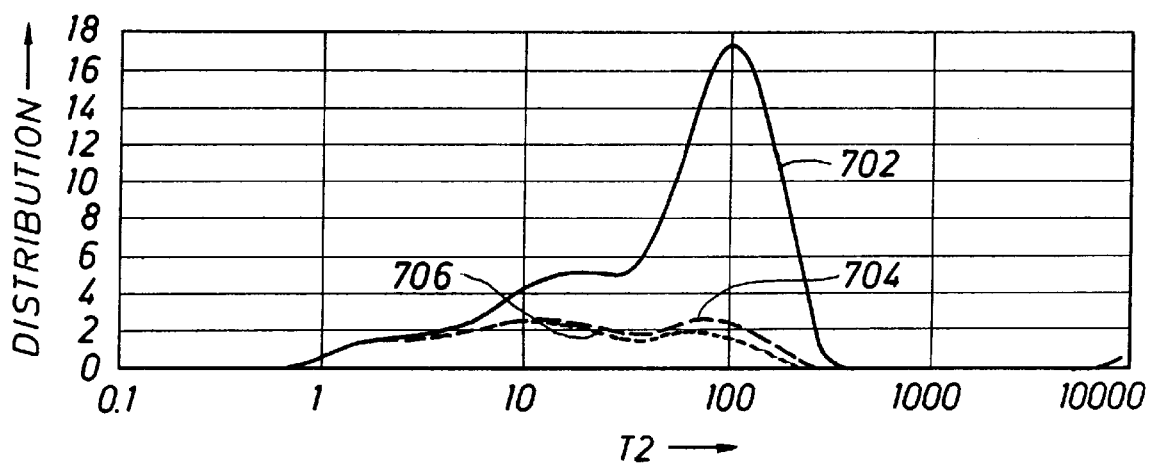
FIG. 7 is a graph showing another comparison of $T_2$ distributions for a high permeability sample as determined for an empirical tapered cutoff analysis (i.e., Coates empirical analysis) and for a partial polarization analysis in accordance with the present invention.

FIG. 7 shows an original $T_2$ distribution for a high permeability sample compared to an empirical tapered $T_2$ cutoff calculation and a partial polarization distribution (in accordance with equation 9) in $T_2$. Curve 702 represents an actual laboratory $T_2$ distributions obtained from a sandstone sample. NMR analysis of the sample showed it to have a porosity of 33.70 pu and a permeability of 154.36 md. Curve 704 represents an empirical tapered cutoff calculation of $T_2$ based on m=0.0618 and b=1. Curve 704 results in an empirical tapered $T_2$ cutoff calculation for BFV of 9.14 pu. Curve 706 represents a partial polarization distribution (in accordance with equation 9) in $T_2$ with a wait time $t_r$ of 15 milliseconds. Curve 706 results in a partial polarization calculation in $T_2$ for BFV of 8.18 pu—within 0.96 pu of the value for the tapered $T_2$ cutoff. Thus, for both high and low permeability formations, the BFV results from an empirically determined tapered $T_2$ cutoff and partial polarization in $T_2$ still are within 1 pu of each other.

Figure 8:
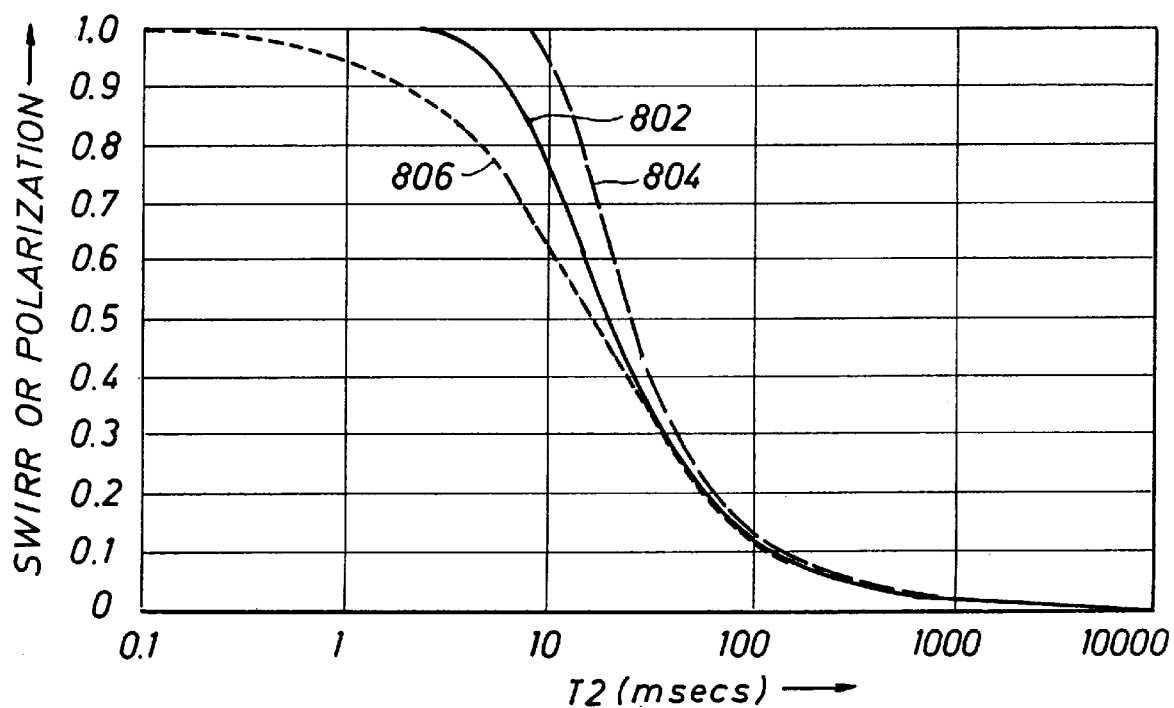
FIG. 8 is a graph showing a comparison of the cutoff that is produced by the partial polarization techniques of the present invention versus theoretical (i.e., Kleinberg theoretical analysis) and empirical (i.e., Coates empirical analysis) tapered cutoff.

FIG. 8 shows polarization versus $T_2$ for a partial polarization distribution (plotted in accordance with equation 9) on curve 802. Curve 804 represents a tapered $T_2$ cutoff derived theoretically based on T'=0.22*33 (msec), while curve 806 represents a tapered $T_2$ cutoff derived empirically based on m=0.0618 and b=1. FIG. 8 clearly shows the correlation between the theoretical and empirical tapered $T_2$ cutoffs and the partial polarization cutoff according to the present invention in $T_2$ when $t_r$ equals 20 milliseconds and the $T_1/T_2$ ratio is equal to 1.5. In fact, it should be noted that the curve of the partial polarization calculation in $T_2$ lies almost equally between the two tapered cutoff curves.

FIG. 9 is a flow chart illustrating steps for another embodiment of determining bound fluid volume (BFV) in accordance with the principles of the present invention. The inventive principles set forth with respect to FIG. 9 may be combined with the steps shown and described with respect to FIG. 1 above, or they may be carried out in a "single" NMR experiment that assumes the NMR tool is already in the borehole. Instead of choosing a single shortened wait time $t_r$, which may have been inappropriate for a given formation, a series of shortened wait times are selected and applied as a "multi-wait sequence NMR experiment" (if an inappropriate shortened wait time is chosen and full $T_2$ distributions were not obtained, the well log cannot simply be rerun with a modified shortened wait time to produce the desired data). The shortened wait times in the multi-wait sequence are chosen to provide a smooth interpolation between them so that the redundancy of the acquired data provides adequate precision.

For example, assuming that the selected shortened wait time for an NMR experiment according to FIG. 1 is 20 milliseconds, a multi-wait sequence NMR experiment would apply three NMR "sub-experiments" at 10, 20 and 30 milliseconds as follows. In step 910, the static magnetic field is applied for 10 milliseconds, at which time, in step 912, the oscillating magnetic field is applied. The induced signals are detected in step 914 and analyzed in step 916 (which is substantially similar to step 116 described above) to produce $AMP_{MAX10}$. The result is stored in a step 920. A test is performed in step 922 to determine whether additional sub-experiments are to be run (in this instance, two more sub-experiments are to be run, one for 20 milliseconds and one for 30 milliseconds). Steps 910 through 920 are carried out again utilizing 20 milliseconds and 30 milliseconds as the shorted wait time to produce $AMP_{MAX20}$ and $AMP_{MAX30}$, respectively. Finally, in step 924, $AMP_{MAX}$, $AMP_{MAX20}$ and $AMP_{MAX30}$ are interpolated and $AMP_{MAX}$ is output. Persons skilled in the art will appreciate that the multi-wait sequence of FIG. 9 may be utilized using more or less than the three shortened wait times described herein (for example, four shortened wait times).

It will be understood that the foregoing is only illustrative of the principles of the invention, and that various modifications can be made by those skilled in the art without departing from the scope and spirit of the invention.

We claim:

1. A method of determining the amount of bound fluid in an earth formation utilizing a nuclear magnetic resonance (NMR) tool that is placed in a borehole in the formation and which produces a static magnetic field and an oscillating magnetic field according to a pulse sequence, and measures induced magnetic signals, the method comprising:

applying the static magnetic field from the NMR tool to a volume of the formation;

applying the oscillating magnetic field to the volume of the formation for a plurality of pulse sequences, each pulse sequence being preceded by a shortened wait time, without an extensive wait time for full polarization, so that the static magnetic field only partially polarizes the volume of formation and induces signals only from bound fluid in the volume of formation;

measuring the induced signals; and determining the amplitude of the induced signals, the amplitude being representative of the amount of bound fluid in the formation.

2. The method of claim 1, wherein applying the oscillating magnetic field comprises:

applying an excitation pulse that turns magnetization into a transverse plane.

3. The method of claim 2, wherein applying the oscillating magnetic field further comprises:

applying less than ten refocusing pulses to induce magnetic signals in the volume of the formation.

4. The method of claim 2, wherein applying the oscillating magnetic field further comprises:

applying a single refocusing pulse to induce magnetic signals in the volume of the formation.

5. The method of claim 1, wherein the induced magnetic signals comprise spin-echos, and measuring comprises recording the spin-echos.

6. The method of claim 5, wherein determining comprises:

analyzing each of the recorded spin-echos to determine the amplitude of each spin-echo.

7. The method of claim 6, wherein determining further comprises:

analyzing the measured spin-echos and extrapolating backward to time zero to produce the signal representative of the bound fluid in the volume of formation.

8. The method of claim 1, wherein the shortened wait time is substantially less than $T_{1MAX}$.

9. The method of claim 1, wherein the shortened wait time is selected so that a partial polarization cutoff curve substantially matches a tapered cutoff curve.

10. The method of claim 9, wherein the tapered cutoff curve is determined based on Kleinberg's theoretical analysis.

11. The method of claim 9, wherein the tapered cutoff curve is determined based on Coates's empirical analysis.

12. The method of claim 9, wherein the partial polarization cutoff curve is based on $T_1$ Effect as a function of $T_1$ and the shortened wait time is adjusted in order for the $T_1$ Effect to match a cutoff curve/value in $T_1$.

13. The method of claim 9, wherein the partial polarization cutoff curve is based on $T_1$ Effect as a function of $T_2$, a $T_1/T_2$ ratio selected based on the formation lithology and the shortened wait time is adjusted in order for the $T_1$ Effect to match a cutoff curve/value in $T_2$.

14. A method of determining the amount of bound fluid in an earth formation utilizing a nuclear magnetic resonance (NMR) tool that is placed in a borehole in the formation and which produces a static magnetic field and an oscillating magnetic field according to a pulse sequence, and measures induced magnetic signals while drilling the borehole, the method comprising:

drilling the borehole;

applying, while drilling the borehole, the static magnetic field from the NMR tool to a volume of the formation;

applying, while drilling the borehole, the oscillating magnetic field to the volume of the formation for a plurality of pulse sequences, each pulse sequence being preceded by a shortened wait time, without an extensive wait time for full polarization, so that the static magnetic field only partially polarizes the volume of formation and induces signals only from bound fluid in the volume of formation;

measuring, while drilling the borehole, the induced signals; and determining the amplitude of the induced signals, the amplitude being representative of the amount of bound fluid in the volume of the formation.

15. The method of claim 14, wherein applying the oscillating magnetic field comprises:

applying an excitation pulse that turns magnetization into a transverse plane.

16. The method of claim 15, wherein applying the oscillating magnetic field further comprises:

applying less than ten refocusing pulses to induce magnetic signals in the volume of the formation.

17. The method of claim 15, wherein applying the oscillating magnetic field further comprises:

applying a single refocusing pulse to induce magnetic signals in the volume of the formation.

18. The method of claim 14, wherein the induced magnetic signals comprise spin-echos, and measuring comprises recording the spin-echos.

19. The method of claim 18, wherein determining comprises:

analyzing each of the recorded spin-echos to determine the amplitude of each spin-echo.

20. The method of claim 19, wherein determining further comprises:

analyzing the spin-echos and extrapolating backward to time zero to produce the signal representative of the bound fluid in the volume of formation.

21. The method of claim 14, wherein the shortened wait time is substantially less than $T_{1MAX}$.

22. The method of claim 14, wherein the shortened wait time is selected so that a partial polarization cutoff curve substantially matches a tapered cutoff curve.

23. The method of claim 22 wherein the tapered cutoff curve is determined based on Kleinberg's theoretical analysis.

24. The method of claim 22, wherein the tapered cutoff curve is determined based on Coates's empirical analysis.

25. The method of claim 22, wherein the partial polarization cutoff curve is based on $T_1$ Effect as a function of $T_1$ and the shortened wait time is adjusted in order for the $T_1$ Effect to match a cutoff curve/value in $T_1$.

26. The method of claim 22, wherein the partial polarization cutoff curve is based on $T_1$ Effect as a function of $T_2$, a $T_1/T_2$ ratio selected based on the formation lithology and the shortened wait time is adjusted in order for the $T_1$ Effect to match a cutoff curve/value in $T_2$.

27. A method of determining the amount of bound fluid in an earth formation utilizing a nuclear magnetic resonance (NMR) tool that is placed in a borehole in the formation and which produces a static magnetic field and an oscillating magnetic field according to a pulse sequence, and measures induced magnetic signals, the method comprising:

applying the static magnetic field from the NMR tool to a volume of the formation to create longitudinal magnetization by aligning proton spins with the static magnetic field;

applying the oscillating magnetic field to the volume of the formation in the form of a pulse sequence that is preceded by a shortened wait time, without an extensive wait time for full polarization, defined by the time the spins enter the static magnetic field so that the static magnetic field only partially polarizes the volume of formation and induces signals only from bound fluid in the volume of formation;

measuring the induced signals; and determining the amplitude of the induced signals, the amplitude being representative of the amount of bound fluid in the volume of the formation.

28. A method of determining the amount of bound fluid in an earth formation utilizing a nuclear magnetic resonance (NMR) tool that is placed in a borehole in the formation and which produces a static magnetic field and an oscillating magnetic field according to a pulse sequence, and measures induced magnetic signals while drilling the borehole, the method comprising:

drilling the borehole;

applying, while drilling the borehole, the static magnetic field from the NMR tool to a volume of the formation to create longitudinal magnetization by aligning proton spins with the static magnetic field;

applying, while drilling the borehole, the oscillating magnetic field to the volume of the formation in the form of a pulse sequence that is preceded by a shortened wait time, without an extensive wait time for full polarization, defined by the time the spins enter the static magnetic field so that the static magnetic field only partially polarizes the volume of formation and induces signals only from bound fluid in the volume of formation;

measuring, while drilling the borehole, the induced signals; and determining the amplitude of the induced signals, the amplitude being representative of the amount of bound fluid in the volume of the formation.

29. A method of determining the amount of bound fluid in an earth formation utilizing a nuclear magnetic resonance (NMR) tool that is placed in a borehole in the formation and which produces a static magnetic field and an oscillating magnetic field according to a pulse sequence, and measures induced magnetic signals, the method comprising:

selecting a series of shortened wait times;

for each shortened wait time in the series:

applying the static magnetic field from the NMR tool to a volume of the formation;

applying the oscillating magnetic field to the volume of the formation for a sequence of pulses, the pulse sequence being preceded by the shortened wait time, without an extensive wait time for full polarization, so that the static magnetic field only partially polarizes the volume of formation and induces signals only from bound fluid in the volume of formation;

measuring the induced signals;

determining the amplitude of the induced signals; and storing the amplitude; and interpolating all of the stored amplitudes to produce an amplitude that is representative of the amount of bound fluid in the volume of the formation.

* * * * *